(12) United States Patent
Israelson

(10) Patent No.: US 11,083,618 B2
(45) Date of Patent: Aug. 10, 2021

(54) ASSEMBLY COMPRISING AN OSTOMY DEVICE AND A PACKAGE FOR THE OSTOMY DEVICE

(71) Applicant: Coloplast A/S, Humlebaek (DK)

(72) Inventor: Dorrit Diana Israelson, Espergaerde (DK)

(73) Assignee: Coloplast A/S, Humlebaek (DK)

( * ) Notice: Subject to any disclaimer, the term of this patent is extended or adjusted under 35 U.S.C. 154(b) by 603 days.

(21) Appl. No.: 15/579,220

(22) PCT Filed: Jun. 3, 2016

(86) PCT No.: PCT/DK2016/050163
§ 371 (c)(1),
(2) Date: Dec. 4, 2017

(87) PCT Pub. No.: WO2016/192738
PCT Pub. Date: Dec. 8, 2016

(65) Prior Publication Data
US 2018/0177626 A1 Jun. 28, 2018

(30) Foreign Application Priority Data
Jun. 4, 2015 (DK) .......................... PA 2015 70350

(51) Int. Cl.
*A61F 5/443* (2006.01)
*A61B 50/30* (2016.01)
(Continued)

(52) U.S. Cl.
CPC .............. *A61F 5/443* (2013.01); *A61B 50/30* (2016.02); *A61F 5/445* (2013.01); *A61B 2050/0056* (2016.02); *A61B 2050/0065* (2016.02)

(58) Field of Classification Search
CPC ........ A61F 5/443; A61F 5/445; A61F 15/001; A61F 15/002; A61F 2013/00897; A61B 5/68335; A61B 2050/0065; A61B 2050/005; A61B 50/30; A61B 50/33; A61B 2050/0056; A61J 1/00
See application file for complete search history.

(56) References Cited

U.S. PATENT DOCUMENTS

| 2,969,145 A | 1/1961 | Hannauer |
| 3,017,990 A | 1/1962 | Singerman |

(Continued)

FOREIGN PATENT DOCUMENTS

| CN | 1332620 A | 1/2002 |
| CN | 104661621 A | 5/2015 |

(Continued)

*Primary Examiner* — Tatyana Zalukaeva
*Assistant Examiner* — Heather K Barnwell
(74) *Attorney, Agent, or Firm* — Coloplast Corp., Coloplast A/S; Nick Baumann

(57) ABSTRACT

An assembly for an ostomy device has a ring of adhesive disposed in a package. The package has a first and a second package portion. The package portions are interconnected in such a way that the package is in a closed state when the first and second package portions are in a first mutual position, and in an open state when the first and second package portions are in a second mutual position. The assembly has a release liner provided to cover a front surface of the ring of adhesive.

11 Claims, 3 Drawing Sheets

(51) Int. Cl.
    *A61F 5/445*    (2006.01)
    *A61B 50/00*    (2016.01)

(56)         References Cited

U.S. PATENT DOCUMENTS 5,333,753 A *    8/1994  Etheredge ............. A61F 15/001
                                                        206/441
    6,149,614 A     11/2000  Dunshee et al.
    6,700,033 B1     3/2004  Marcussen et al.
 2007/0173752 A1    7/2007  Schonfeldt
 2014/0163496 A1*   6/2014  Grum-Schwensen .......................
                                                     A61F 5/443
                                                        604/338
 2014/0303574 A1   10/2014  Knutson

FOREIGN PATENT DOCUMENTS

JP      2003024370 A    1/2003
    KR     20120129145 A   11/2012
    RU        2519961 C2    6/2014
    WO         0040183 A1   7/2000
    WO      2013014231 A1   1/2013
    WO      2014020095 A1   2/2014

* cited by examiner

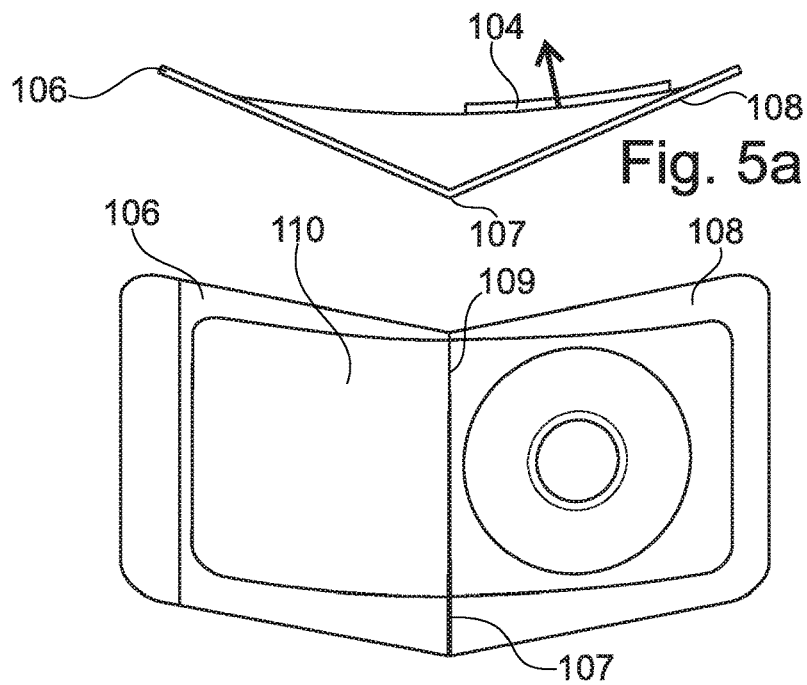
Fig. 5a
Fig. 5b
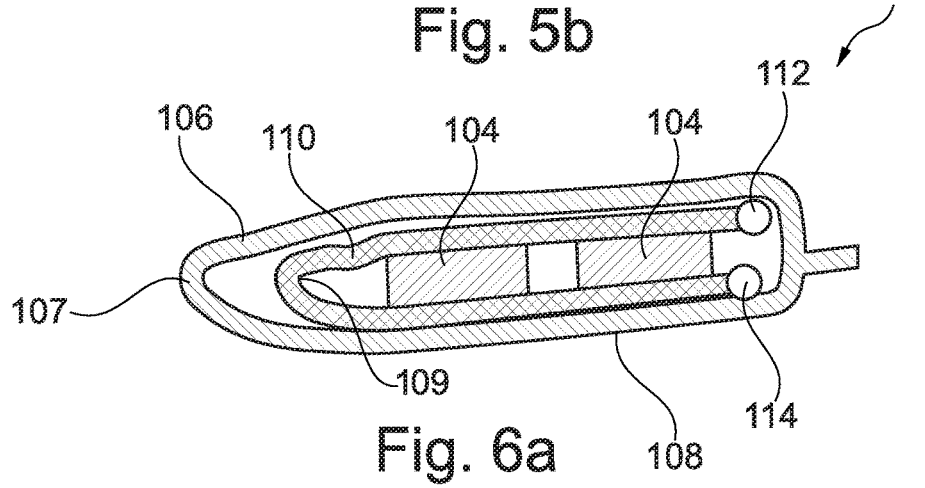
Fig. 6a
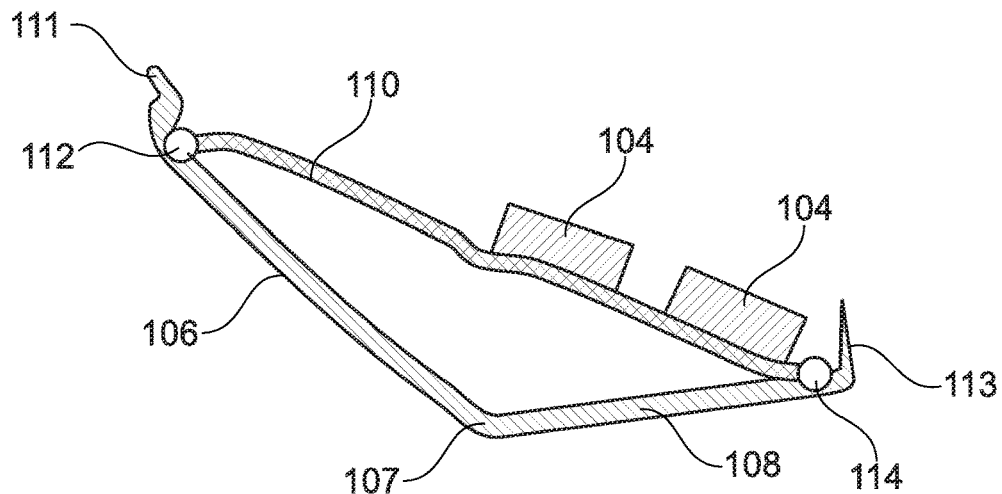
Fig. 6b

ASSEMBLY COMPRISING AN OSTOMY DEVICE AND A PACKAGE FOR THE OSTOMY DEVICE

TECHNICAL FIELD

The present invention relates to an assembly comprising an ostomy device and a package for the ostomy device, and to a method for removing an ostomy device from a package therefor. The ostomy device may in particular comprise or be constituted by a mouldable adhesive barrier ring for an ostomy appliance, but may additionally or alternatively also include an ostomy wafer.

BACKGROUND OF THE INVENTION

Ostomy systems typically comprise a wafer, also referred to as a base plate, comprising an adhesive area surrounding an opening for accommodating the patient's stoma. Further, ostomy systems may comprise an adhesive, i.e. tacky, barrier ring which is mouldable by hand to provide a customized liquid-tight fit around the patient's stoma.

Ostomy systems may include a one-piece or a two-piece system. Both kinds include an adhesive wafer and a collection pouch. The pouch attaches to the abdomen by the adhesive wafer and is fitted over and around the stoma to collect body waste. The wafer and its adhesive are designed to protect the skin from the stoma output and to be as skin-friendly as possible. Two-piece systems allow pouches to be changed while leaving the wafer attached to the skin, whereas in one-piece systems the pouch and wafer come as a single integrated unit, which is to be replaced in its entirety when the pouch is changed.

Wafers for two-piece systems may be supplied separately to patients separately from pouches, and for both types of systems, barrier rings may be supplied to patients separately from wafers and pouches. Barrier rings are typically supplied in a package with a release liner covering at least one surface thereof.

The barrier ring is typically made from a soft, ductile and tacky material, the removal of which from a package may be difficult, in particular if the barrier is arranged in a cavity of a package with a cylindrical centre element protruding into the ring, as is often the case. Additionally, some patients suffer from reduced dexterity and may hence encounter difficulties when handling barrier rings and wafers, notably when peeling the release liner off the barrier ring or wafer and when removing the tacky barrier ring from its package. Further disposing of the release liners once peeled off poses a practical problem, in particular due to the fact that the patient or nurse handling and mounting the barrier ring or wafer is compelled to use two hands for positioning and moulding the barrier ring or wafer immediately after its separation from the release liner. Additionally a release liner may build up static electricity which may be a nuisance if it is initially lost and subsequently picked up for disposing thereof.

SUMMARY OF THE INVENTION

On the above background it is an object of embodiments of the present invention to provide an assembly comprising an ostomy device and a package therefor which is easy to handle, as well as a convenient method for removing an ostomy device from the package. It is a further object of embodiments of the invention to facilitate disposal of release liners of ostomy barrier rings and ostomy wafers. It is a further object of embodiments of the invention to reduce nuisances caused by build-up of static electricity at release liners once the release liners have been separated from ostomy barrier rings and wafers.

In a first aspect the invention provides an assembly comprising an ostomy device and a package for the ostomy device, wherein:
 the ostomy device comprises an adhesive front surface;
 the package comprises at least a first and a second package portion which are interconnected in such a way that the package is in a closed state when the first and second package portions are in a first mutual position and such that the package is in an open state when the first and second package portions are in a second mutual position, wherein the package forms an enclosure for the ostomy device when the package is in the closed state; and wherein:
 the assembly further comprises a release liner which at least partially covers the adhesive front surface of the ostomy device at least in the closed state of the package; and
 at least a portion of the release liner is attached to the package or formed integrally therewith.

In a second aspect the invention provides a method for removing an ostomy device from a package therefor, wherein
 the ostomy device comprises an adhesive front surface;
 the package comprises at least a first and a second package portion which are interconnected in such a way that the package is in a closed state when the first and second package portions are in a first mutual position and such that the package is in an open state when the first and second package portions are in a second mutual position, wherein the package forms an enclosure for the ostomy device when the package is in the closed state;
 the assembly further comprises a release liner which at least partially covers the adhesive front surface of the ostomy device at least in the closed state of the package; and wherein
 at least a portion of the release liner is attached to the package or formed integrally therewith; the method comprising the steps of:
 opening the package by relative movement of the first and second package portions from the first mutual position to the second mutual position;
 removing the ostomy device from the package by detaching the ostomy device from the release liner while the release liner remains attached to or integral with the package.

Thanks to the attachment of the release liner to the package, or its integration with the package, the release liner may remain attached to or integral with the package even after separation of the release liner from the ostomy device. Hence, the release liner can be disposed of together with the package, and build-up of static electricity may be reduced. Furthermore, the release liner may be attached to the package in such a way that it at least partially detaches from the ostomy device by the relative movement of the first and second package portions when the user opens the package. The release liner may in particular be attached to or formed integrally with at least one of the first and second package portions, whereby movement of one the package portions relative to the other one causes relative movement between the release liner and the ostomy device to at least partially peel off the release liner from the adhesive front surface of the ostomy device. The release liner is preferably attached to or integral with one or more interior parts of the package, i.e. parts of the package facing inwardly when the package is closed.

The release liner may be attached to the package by welding or by adhesive, such as hotmelt or PSA double layer tape or like bonding means.

The ostomy device may in particular comprise or be constituted by a mouldable adhesive (i.e. tacky) ring for an ostomy appliance, i.e. a so-called barrier ring, but may additionally or alternatively also include an ostomy wafer. In one embodiment, the ostomy device may include a wafer, such as for a one-piece or a two-piece ostomy system, carrying the barrier ring as part thereof. The mouldable adhesive barrier ring may be mouldable by hand to provide a customized liquid-tight fit around the patient's stoma. The invention has been found to be particularly beneficial in respect of embodiments in which the ostomy device comprises a mouldable adhesive ring, i.e. a tacky so-called barrier ring typically made from a ductile and soft paste, as handling of such a ring, including its removal from a package in which it is supplied, may be associated with difficulties, not only to users suffering from reduced dexterity. Such difficulties may be avoided or reduced by embodiments of the present invention, in which the barrier ring may be freely exposed after opening of the package. Further, it has been found that the geometry and size of the mouldable adhesive ring is particularly suitable for use with a release liner which is attached to or integral with the package for the ring.

The ostomy device may for example include an ostomy paste ring, a barrier ring, and an ostomy artificial skin pad, or a wafer.

Generally, the ostomy device, in particular mouldable adhesive barrier ring, may comprise a back surface opposite to the adhesive front surface. The back surface may be tacky but need not be so. The release liner may conveniently be folded and sized so that it further at least partially covers the back surface, or alternatively a separate release liner may be provided for covering the back surface. Hence while the release liner detaches from one of the front and back surface when the package is opened, the same or another release liner may remain attached to the other surface. In that manner both of the opposed surfaces of the ostomy device are protected by the one or more release liners during storage thereof in the package, and it is ensured that the ostomy device is easily removable from the package after opening thereof by separating the back surface of the ostomy device from the back surface release liner portion. The release liner or release liner system may comprise any number of sheets and supporting sheets from, e.g. paper or plastics foil.

In a particularly convenient embodiment, the release liner extends along the front and the back surface, it being formed from a single sheet of material, which is folded to cover both surfaces or parts thereof.

It should be understood that the release liners disclosed herein may cover the entire front surface and/or the entire back surface of the ostomy device. Whereas, as mentioned above, one single sheet of release liner may be provided which covers the entire front surface and the entire back surface, separate release liner sheets may alternatively be provided. For example, separate release liner sheets may be provided for the front and the back surfaces, respectively, or a plurality of release liner sheets may be provided at each of the front and/or back surfaces.

Due to the tack between the back surface of the ostomy device and the release liner at the back surface, a dedicated centre portion, such as a cylindrical element protruding from a surface of the package, may be avoided for fixating the ostomy device relative to the package during storage thereof. Thus, a centre opening in the ostomy device, typically in the form of a centre hole, is immediately accessible for the user's fingers for handling of the ostomy device, in particular for removing of the ostomy device from the package. This is particularly advantageous in case of a soft, ductile and tacky barrier ring.

The package, including the first and second package portions, may form a hard casing for the ostomy device. Alternatively, the package potions may be made from a pliant material. A hard casing is preferred because the package in that case may provide mechanical protection to and structural support for the ostomy device, notably for a mouldable adhesive ring which may be pliant and not necessarily self-supporting. The package preferably forms a closed enclosure for the ostomy device.

Generally, the package may be provided to protect the ostomy device from contamination and external mechanical pressure. The package may have any suitable geometry, such as circular, elliptical, rectangular, square, etc. The package, notably the first and second package portions may be made from any suitable material, such as cardboard, carton paper, wood, polymer foams, polymer films, injection moulded plastics, etc.

In one embodiment each of the first and second package portions forms a package half, the package halves being e.g. pivotally interconnected along respective edges. The package may thus form a book-like (or leaflet-like) structure with mating edges of the respective first and second package portions forming a linearly extending hinge between them. The first and second package portions, i.e. the package halves, may be integrally formed from a single piece of material, such as a plastics material with the hinge being provided as a weakened line in the material. Alternatively, the halves may constituted separate parts which have been assembled subsequent to manufacture of the parts.

To render the release liner easily accessible to the user upon opening of the package, the release liner may be attached to or integral with at least one of the first and second package portions in such a way that it at least partially detaches from the adhesive front surface of the ostomy device when the package is opened by relative movement of the first and second package portions from the first mutual position to the second mutual position.

In one embodiment of the invention, the first package portion may provide a package bottom part which forms a supporting surface for the back surface of the ostomy device, and the second package portion may form a lid of the package. In such embodiment, the release liner may be attached to or integral with an interior surface of any one of the bottom and lid parts. For example, the release liner may be attached to or integral with the bottom part only, or it may be attached to or integral with the bottom part and the lid.

DESCRIPTION OF EMBODIMENTS OF THE INVENTION

Embodiments of the invention will now be described further with reference to the accompanying drawings, in which:

FIG. 5a is a side view of the assembly during opening of the package;

FIG. 5b is a top side view of the assembly with the package opened;

FIG. 6a is a side cross-sectional view of one embodiment of an assembly including a package enclosing an ostomy device, and the package in a closed position;

FIG. 6b is a side cross-sectional view of the assembly of FIG. 6a with the package in an opened position;

Figure 1:
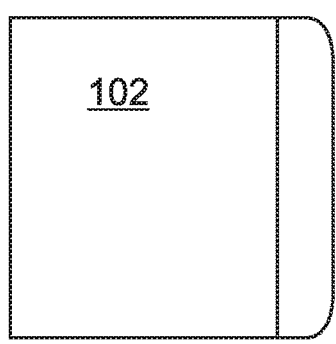
FIG. 1 is a top side view of one embodiment of an assembly including a package enclosing an ostomy device.

The respective embodiments of the assemblies 100 of FIGS. 1-8b comprise a package 102 for an ostomy device which is illustrated in the form of an adhesive mouldable barrier ring 104. The package 102 comprises a first package portion 106 and a second package portion 108, which are mutually interconnected along hinge or pivot 107. The first package portion 106 defines a lid for the package, whereas the second package portion 108 forms a bottom part of the package. The barrier ring 104 is supported by a release liner 110. In all of the embodiments shown in the drawings, the release liner 110 is folded at 109 around the barrier ring 104 when the package is in its closed state as shown in FIGS. 1, 6a, 7a and 8a, whereby the release liner 110 covers a front surface (facing upwardly in the drawings) of the barrier ring 104 as well as a back surface thereof (turning downwardly in the drawings).

In the embodiments of FIGS. 1-6b, the release liner 110 is attached to inner surfaces of both the first and second package portions 106, 108. In FIGS. 6a and 6b, the points of attachments are indicated at 112 and 114.

Figure 2:
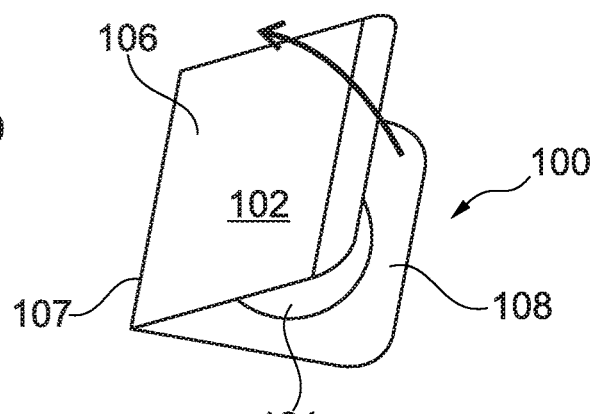
FIG. 2 is a perspective view of the assembly showing the ostomy device inside of the package.
Figure 3:
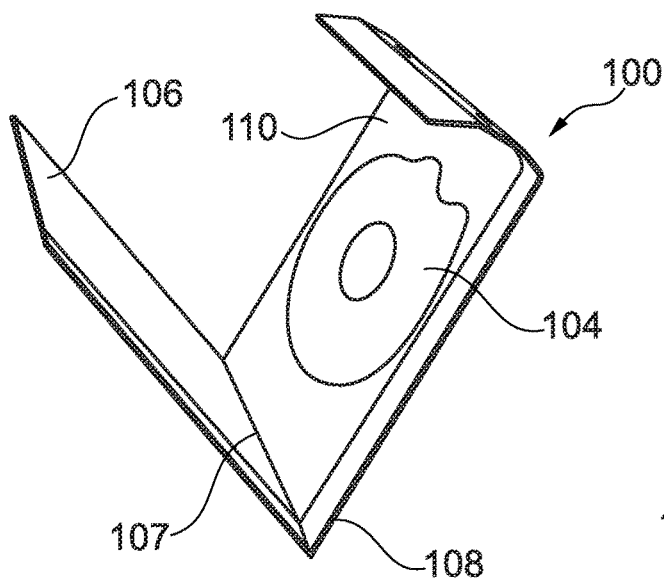
FIG. 3 is a perspective view of the assembly as the package is opened.
Figure 4:
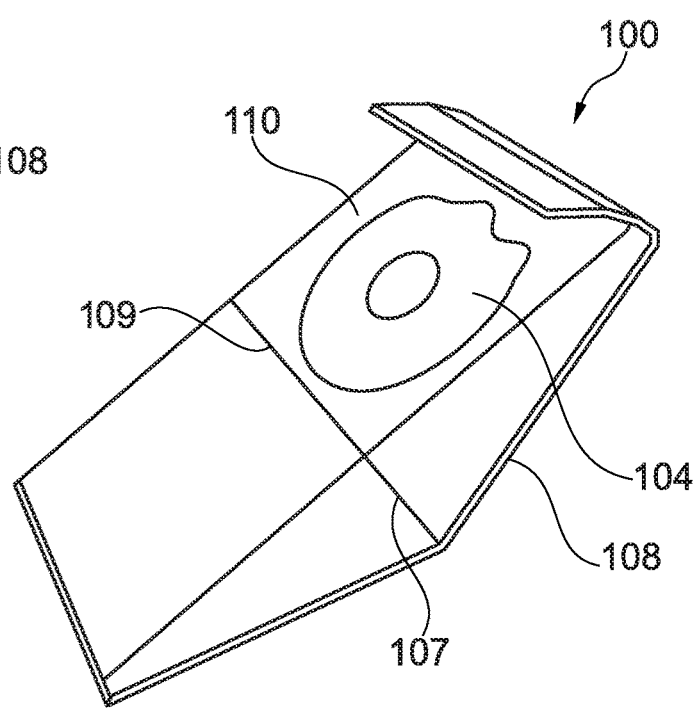
FIG. 4 is a perspective view of the assembly during use.

Mutual movement of the first package portion 106 relative to the second package portion 108 is effected by rotation of the first package portion 106 around the hinge or pivot 107, as indicated by arrow in FIG. 2. Upon initial opening of the package, the assembly attains the configuration shown in FIG. 2, in which the release liner 110 has been detached from the front surface of the barrier ring 104. Further opening of the package causes the release liner 110 to lift off from the inner surfaces of the package portions 106, 108, as indicated by arrow in FIG. 5a and shown in FIGS. 5a and 5b. The barrier ring 104 thus facing upwardly on top of the release liner 110 is hence readily accessible to the user and may be peeled off the release liner 110, while the release liner 110 remains attached to the package portions 106 and 108.

Figure 7A:
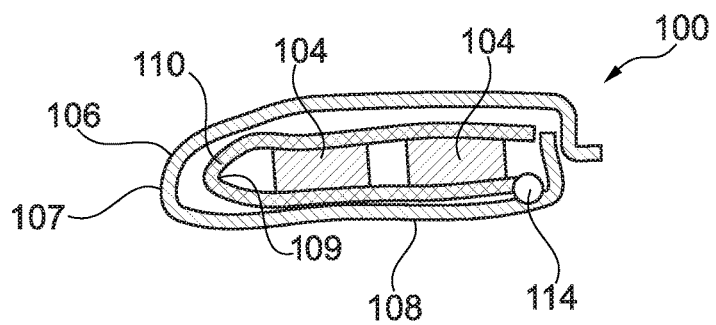
FIG. 7a is a side cross-sectional view of one embodiment of an assembly including a package enclosing an ostomy device, with the package in a closed position.
Figure 7B:
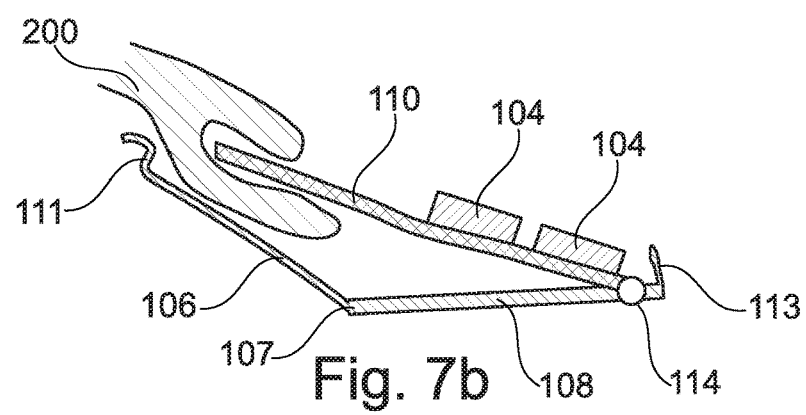
FIG. 7b is a side cross-sectional view of the assembly of FIG. 7a with the package in an opened position.

In the embodiment of FIGS. 7a and 7b, the release liner 110 is attached to the second package portion 108 only, i.e. to the bottom package part, at 114. More particularly, the release liner 110 is attached to the bottom package part 108 at an edge thereof opposite the hinge or pivot 107. Thus upon opening of the package, the release liner 110 remains attached to the upper surface of the barrier ring 104, i.e. remains in the position shown in FIG. 7. The user manually peels the release liner 110 off the upper surface and subsequently places his or her hand 200 as shown in FIG. 7b to expose the barrier ring 104 for further handling, i.e. removal from the package thereof.

Figure 8A:
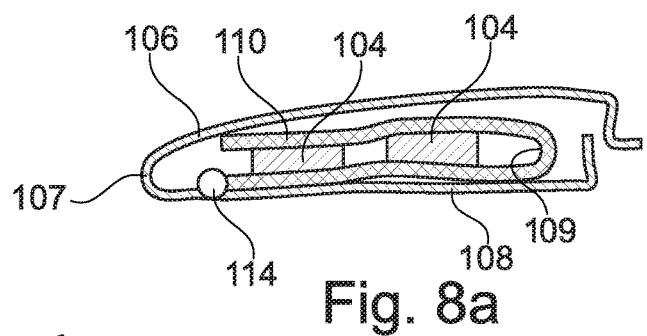
FIG. 8a is a side cross-sectional view of one embodiment of an assembly including a closed package enclosing an ostomy device.
Figure 8B:
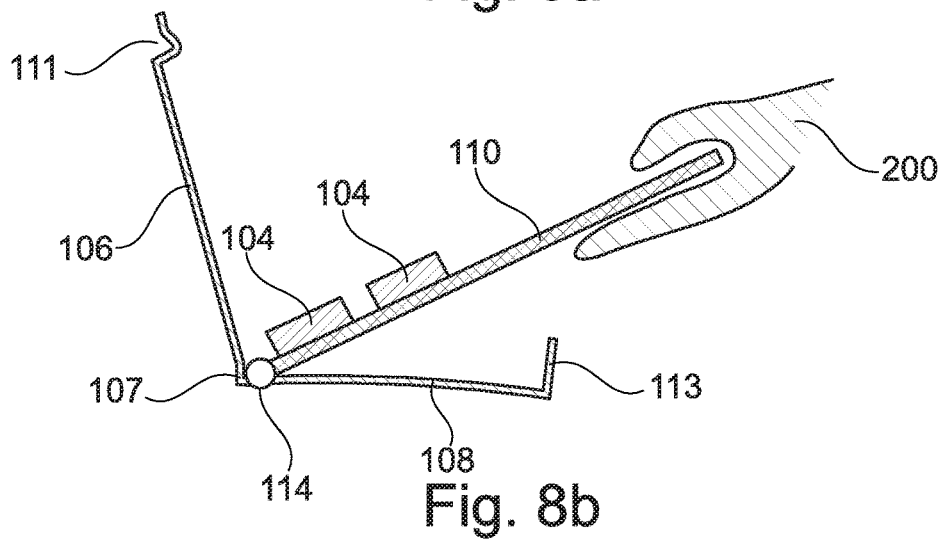
FIG. 8b is a side cross-sectional view of the assembly of FIG. 8a with the package in an opened position.

In the alternative embodiment of FIGS. 8a and 8b, the release liner 110 is also attached to the bottom package portion 108 only, at 114, however at the edge near the hinge or pivot 107. As in the embodiment of FIGS. 7a and 7b, in FIGS. 8a and 8b the release liner 110 remains attached to the upper surface of the barrier ring 104, i.e. remains in the position shown in FIG. 8a when the lid package portion 106 is flipped over. The user manually peels the release liner 110 off the upper surface and subsequently places his or her hand 200 as shown in FIG. 8b to expose the barrier ring 104 for further handling, i.e. removal from the package thereof.

In the embodiments of FIGS. 6a-8b, the upper and lower package portions 106, 108 form a hard casing, with the lower package portion 108 defining a side wall 113, and the upper package portion 106 defining a combined side wall and grip handle 111 for effecting separation of the package portions and opening of the package.

The invention claimed is:

1. An ostomy assembly comprising:
a ring of adhesive comprising a front surface and a back surface with a hole formed through the ring of adhesive extending through the front surface and the back surface, with the hole sized for placement around a stoma of a user;
a package comprising a first portion that is secured to a second portion to form a closed package enclosing the ring of adhesive; and
a release liner disposed inside of the closed package, with the release liner in direct contact with the front surface of the ring of adhesive and in direct contact with the back surface of the ring of adhesive;
wherein the release liner is connected to an inside surface of the second portion of the closed package.

2. The ostomy assembly of claim 1, wherein the closed package includes a pivot defined where the first portion is interconnected with the second portion.

3. The ostomy assembly of claim 1, wherein the release liner is connected to an inside surface of the first portion of the closed package such that, when the closed package is opened, the release liner is removed away from contact with the front surface of the ring of adhesive.

4. The ostomy assembly of claim 1, wherein the release liner is not connected to the first portion of the closed package such that, when the closed package is opened, the release liner remains in contact with the front surface of the ring of adhesive.

5. The ostomy assembly of claim 1, wherein the closed package includes a pivot defined where the first portion is interconnected with the second portion, and the release liner is connected to the inside surface of the second portion of the closed package at a location that is spaced apart from the pivot by a distance equal to about a length of the second portion of the closed package.

6. The ostomy assembly of claim 1, wherein the closed package includes a pivot defined where the first portion is interconnected with the second portion;
wherein the release liner is connected to an inside surface of the first portion of the closed package at a first location and is connected to the inside surface of the second portion of the closed package at a second location, with the pivot located about equidistant away from the first location and the second location.

7. The ostomy assembly of claim 1, wherein the first portion of the closed package includes a combined first side wall and a grip, and the second portion of the closed package includes a second side wall, and the grip allows separation of the first side wall from the second side wall to open the closed package.

8. The ostomy assembly of claim 1, wherein the release liner is adapted to detach from the front surface of the ring of adhesive when the closed package is opened by relative movement of the first portion away from the second portion.

9. The ostomy assembly of claim 1, wherein the release liner is adapted to remain in contact with the front surface of the ring of adhesive when the closed package is opened by relative movement of the first portion away from the second portion.

10. The ostomy assembly of claim 1, wherein the release liner includes a fold located between a first region where the release liner is in contact with the front surface of the ring of adhesive and a second region where the release liner is in contact with the back surface of the ring of adhesive.

11. An ostomy assembly comprising:
   a ring of adhesive comprising a front surface and a back surface with a hole formed through the ring of adhesive extending through the front surface and the back surface, with the hole sized for placement around a stoma of a user;
   a package comprising a first portion that is secured to a second portion to form a closed package enclosing the ring of adhesive; and
   a release liner disposed inside of the closed package, with the release liner folded at a fold line to have a first face in contact with the front surface of the ring of adhesive and a second face in contact with the back surface of the ring of adhesive;
   wherein the release liner is connected to an inside surface of the second portion of the closed package;
   wherein the ostomy assembly is adapted such that, when the closed package is opened, the first face of the release liner is removed away from contact with the front surface of the ring of adhesive.

* * * * *

UNITED STATES PATENT AND TRADEMARK OFFICE
CERTIFICATE OF CORRECTION

| | |
|---|---|
| PATENT NO. | : 11,083,618 B2 |
| APPLICATION NO. | : 15/579220 |
| DATED | : August 10, 2021 |
| INVENTOR(S) | : Dorrit Diana Israelson |

It is certified that error appears in the above-identified patent and that said Letters Patent is hereby corrected as shown below:

In the Specification

In Column 3, Line 5, delete "hotmelt" and insert -- hot melt --, therefor.

In Column 4, Line 36, delete "constituted" and insert -- constitute --, therefor.

Signed and Sealed this
Fourth Day of July, 2023

Katherine Kelly Vidal
*Director of the United States Patent and Trademark Office*